United States Patent
Ditzel et al.

(10) Patent No.: US 9,499,470 B2
(45) Date of Patent: *Nov. 22, 2016

(54) PROCESS FOR THE CARBONYLATION OF DIMETHYL ETHER

(71) Applicant: BP Chemicals Limited, Middlesex (GB)

(72) Inventors: Evert Jan Ditzel, East Yorkshire (GB); Bogdan Costin Gagea, Berkshire (GB); John Glenn Sunley, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/773,153

(22) PCT Filed: Mar. 6, 2014

(86) PCT No.: PCT/EP2014/054397
§ 371 (c)(1),
(2) Date: Sep. 4, 2015

(87) PCT Pub. No.: WO2014/135663
PCT Pub. Date: Sep. 12, 2014

(65) Prior Publication Data
US 2016/0016881 A1    Jan. 21, 2016

(30) Foreign Application Priority Data

Mar. 8, 2013   (EP) .................................... 13158471

(51) Int. Cl.
| | | |
|---|---|---|
| C07C 67/36 | (2006.01) | |
| C07C 67/37 | (2006.01) | |
| B01J 29/18 | (2006.01) | |
| B01J 29/06 | (2006.01) | |
| B01J 37/00 | (2006.01) | |
| C07C 51/09 | (2006.01) | |

(52) U.S. Cl.
CPC ................ *C07C 67/37* (2013.01); *B01J 29/06* (2013.01); *B01J 29/18* (2013.01); *B01J 37/0009* (2013.01); *B01J 37/0018* (2013.01); *C07C 51/09* (2013.01); *B01J 2229/42* (2013.01)

(58) Field of Classification Search
CPC ....... C07C 67/37; C07C 69/14; C07C 51/09; B01J 2229/14; B01J 2229/18; B01J 2229/42; B01J 29/06; B01J 29/18; B01J 29/185; B01J 29/24; B01J 29/65; B01J 29/70; B01J 29/7015; B01J 29/7026; B01J 29/87; B01J 37/0009; B01J 37/0018; B01J 37/08
See application file for complete search history.

(56) References Cited

FOREIGN PATENT DOCUMENTS

| EP | 1985606 | * 10/2008 |
|---|---|---|
| WO | WO 2006/121778 A1 | 11/2006 |
| WO | WO 2008/132438 A1 | 11/2008 |
| WO | WO2008132438 | * 11/2008 |
| WO | WO2010058149 | * 5/2010 |

OTHER PUBLICATIONS

ISR PCT EP2014 054397, 2014.*

* cited by examiner

*Primary Examiner* — Yevegeny Valenrod
*Assistant Examiner* — Blaine G Doletski
(74) *Attorney, Agent, or Firm* — Nixon & Vanderhye P.C.

(57) ABSTRACT

Process for preparing methyl acetate by the carbonylation of dimethyl ether with carbon monoxide in the presence of hydrogen and a zeolite catalyst. In a first step, the carbonylation is conducted with a carbon monoxide to hydrogen molar ratio of at least 1 and, in a second and subsequent step, the carbonylation is conducted with a hydrogen to carbon monoxide molar ratio of greater than 1.

30 Claims, 4 Drawing Sheets

PROCESS FOR THE CARBONYLATION OF DIMETHYL ETHER

This application is the U.S. national phase of International Application No. PCT/EP2014/054397 filed Mar. 6, 2014 which designated the U.S. and claims priority to European Patent Application No. 13158471.6 filed Mar. 8, 2013, the entire contents of each of which are hereby incorporated by reference.

This invention relates to a process for preparing methyl acetate by the carbonylation of dimethyl ether with carbon monoxide in the presence of a zeolite catalyst and hydrogen.

BACKGROUND OF THE INVENTION

Methyl acetate is used industrially in petrochemical processes, particularly as a feedstock for the production of commodity chemicals such as acetic acid and acetic anhydride.

Crystalline aluminosilicate zeolites are known to catalyse the carbonylation of dimethyl ether to produce methyl acetate. For example, WO 2006/121778 describes a process for the production of a lower aliphatic ester of a lower aliphatic carboxylic acid by carbonylating lower alkyl ethers with carbon monoxide in the presence of a mordenite or ferrierite catalyst under substantially anhydrous conditions.

WO 2008/132438 describes the production of methyl acetate by carbonylating dimethyl ether with carbon monoxide in the presence of zeolite catalysts and hydrogen. According to WO 2008/132438, hydrogen has a beneficial effect on the catalytic productivity and/or stability of the zeolite catalyst at temperatures greater than 240° C. However, processes wherein an equimolar or a molar excess of hydrogen is employed are not exemplified.

SUMMARY OF THE INVENTION

Applicant has found that in zeolite catalysed processes for the carbonylation of dimethyl ether with carbon monoxide which are conducted in the presence of a molar excess of hydrogen (relative to carbon monoxide) results in not only poor initial catalytic performance but also in poor catalytic performance throughout the reaction. In particular, poor catalytic performance in carbonylation reactions conducted under excess hydrogen conditions is demonstrated by zeolite catalysts prepared from synthesis mixtures which do not include organic structure directing agents.

Thus, it would be desirable to provide a process for the preparation of methyl acetate by the carbonylation of dimethyl ether with carbon monoxide in the presence of hydrogen and a zeolite catalyst, and in particular a zeolite catalyst prepared without the aid of an organic structure directing agent, which process enables improved catalytic performance to be achieved under conditions of a molar excess of hydrogen.

Applicant has now found that in carbonylation processes for preparing methyl acetate by carbonylating dimethyl ether with carbon monoxide in the presence of a zeolite catalyst under a molar excess of hydrogen, improved catalytic performance is achieved if the carbonylation process is conducted initially with an equimolar or molar excess of carbon monoxide (relative to hydrogen) and thereafter the carbon monoxide to hydrogen molar ratio is adjusted such that the process is carried out with a molar excess of hydrogen.

Accordingly, the present invention provides a process for preparing methyl acetate by the carbonylation of dimethyl ether with carbon monoxide in the presence of hydrogen and a zeolite catalyst wherein, in a first step the carbonylation is conducted with a carbon monoxide to hydrogen molar ratio of at least 1 and in a second and subsequent step, the carbonylation is conducted with a hydrogen to carbon monoxide molar ratio of greater than 1.

The present invention also provides a process for improving the performance of a zeolite catalyst in the preparation of methyl acetate by the carbonylation of dimethyl ether with carbon monoxide in the presence of hydrogen and said catalyst wherein, in a first step the carbonylation is conducted with a carbon monoxide to hydrogen molar ratio of at least 1 and in a second and subsequent step, the carbonylation is conducted with a hydrogen to carbon monoxide molar ratio of greater than 1.

Advantageously, operation of a carbonylation catalyst and process in accordance with the present invention results in an improvement in catalytic performance, such as activity and/or selectivity compared to carbonylation processes which are operated throughout with a molar excess of hydrogen. Desirably, the present invention can achieve a sustained improvement in catalytic performance throughout the course of the reaction.

BRIEF DESCRIPTION OF THE DRAWINGS

The invention is further described with reference to the accompanying drawings, in which:

FIG. 8 depicts the selectivity (%) to methyl acetate versus time on stream for a carbonylation of dimethyl ether conducted with an initial molar ratio of carbon monoxide:

hydrogen of 4:1 which is thereafter decreased to a molar ratio of 1:2 using a catalyst prepared with an organic structure directing agent.

DETAILED DESCRIPTION OF THE INVENTION

In an embodiment of the present invention, the zeolite has been synthesised from a synthesis mixture which does not comprise an organic structure directing agent.

In another embodiment of the present invention, the first step and second steps are carried out consecutively.

In a further embodiment of the present invention, the first step and second steps are carried out consecutively and the zeolite has been prepared from a synthesis mixture which does not include an organic structure directing agent.

The first step wherein the carbonylation is carried out at a molar ratio of carbon monoxide to hydrogen of at least 1 may hereinafter be referred to as step (i).

The second step wherein the carbonylation is carried out at a molar ratio of hydrogen to carbon monoxide of greater than 1 may hereinafter be referred to as step (ii).

For the avoidance of doubt, the phrase 'a molar ratio of carbon monoxide to hydrogen of at least 1' means that the molar ratio of carbon monoxide/hydrogen is at least 1 and the phrase 'a molar ratio of hydrogen to carbon monoxide of greater than 1' means that the molar ratio of hydrogen/carbon monoxide is greater than 1.

In step (i) the carbonylation is conducted with a carbon monoxide to hydrogen molar ratio of at least 1. This molar ratio provides an equimolar or molar excess of carbon monoxide relative to hydrogen. Without wishing to be bound by theory, it is believed that by initially conducting a carbonylation reaction with at least an equimolar molar amount of carbon monoxide relative to hydrogen, a species of coke is generated on the catalyst's surface which is beneficial in establishing commercially acceptable catalyst selectivities and space time yields.

The carbon monoxide to hydrogen molar ratio in step (i) may be varied, provided it is maintained at a value of at least 1. Suitably, in step (i), the carbon monoxide to hydrogen molar ratio is in the range 1 to 15, such as in the range 2 to 5, for example in the range 2 to 4.

Conveniently, step (i) may be carried out during the start-up of a carbonylation process, wherein the carbonylation is conducted in the presence of fresh catalyst or regenerated catalyst.

The period of time over which step (i) is carried out is somewhat dependent on factors such as the desired space time yields, selectivity and catalyst lifetime. Longer durations generally lead to improved selectivity but reduce catalyst lifetime. Beneficially, the carbon monoxide to hydrogen molar ratio employed in step (i) is decreased on or after stabilisation of the methyl acetate space time yield. Suitably, step (i) is carried out for a period of from about 10 minutes to about 300 hours, for example from about 24 hours to about 250 hours.

Typically, step (i) and step (ii) are carried out consecutively.

After the desired duration of step (i), the molar ratio of carbon monoxide to hydrogen is adjusted such that the carbonylation reaction in step (ii) is conducted with a molar ratio of hydrogen to carbon monoxide which is greater than 1. Suitably, the molar ratio of hydrogen to carbon monoxide in step (ii) is in the range 1.05 to 5, such as in the range 2 to 5, for example 2.

Suitably, the process is carried out wherein in step (i) the molar ratio of carbon monoxide to hydrogen is in the range 1 to 15, such as in the range 1 to 4 or 2 to 5, for example in the range 2 to 4 and wherein in step (ii) the molar ratio of hydrogen to carbon monoxide is in the range 1.05 to 5, for example in the range 2 to 5.

In some or all embodiments of the present invention, the process is carried out wherein in step (i) the molar ratio of carbon monoxide to hydrogen is in the range 1 to 4 and wherein in step (ii) the molar ratio of hydrogen to carbon monoxide is in the range 2 to 5, for example about 2.

Adjustment of the molar ratio of carbon monoxide to hydrogen utilised in step (i) to the molar ratio desired to be employed in step (ii) may suitably be achieved by decreasing the amount of carbon monoxide or by increasing the amount of hydrogen supplied to the carbonylation reaction.

The specific amount of hydrogen supplied to the carbonylation reaction in step (ii) is not critical but it should be sufficient to reduce the carbon monoxide to hydrogen molar ratio of step (i), so as to obtain a molar ratio of hydrogen to carbon monoxide of greater than 1.

If desired, the amount of carbon monoxide introduced into the carbonylation reaction in step (ii) may be reduced so as to decrease the carbon monoxide to hydrogen molar ratio.

The molar ratio of carbon monoxide to hydrogen utilised in step (i) of the carbonylation may be adjusted to that desired for use in step (ii) in a single stage or it may be adjusted gradually, for example in two or more stages, such as two stages. For example where the molar ratio of carbon monoxide to hydrogen in step (i) is 4 and the desired hydrogen to carbon monoxide molar ratio in step (ii) is 2, the carbon monoxide to hydrogen molar ratio can be initially decreased to 2 and thereafter decreased to 0.5 (that is a molar ratio of hydrogen to carbon monoxide of 2).

Where it is desired to decrease the carbon monoxide to hydrogen molar ratio in step (i) in a number of stages, each stage may be commenced after any desired carbonylation reaction time, but suitably each stage is commenced after a reaction time in the range of from about 1 to about 200 hours.

It is not necessary for each stage to be of equal duration.

The carbon monoxide and hydrogen gases utilised in the carbonylation may be substantially pure, for example, carbon monoxide and hydrogen typically provided by suppliers of industrial gases, or they may contain low levels of impurities that do not interfere with the carbonylation reaction, such as methane and carbon dioxide.

Conveniently, a synthesis gas may be used as the source of carbon monoxide and hydrogen. Synthesis gas is a mixture of primarily carbon monoxide and hydrogen in varying amounts but it may also comprise small amounts of carbon dioxide and inert gases and is commercially available. For utilisation in the present invention, a synthesis gas, in addition to carbon monoxide and hydrogen, may comprise one or more of carbon dioxide and inert gases.

Conventional processes for the production of synthesis gas include conversion reactions of hydrocarbon sources such as steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process may include the use of a catalyst, such as catalysts based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

The carbonylation reaction may also be conducted in the presence of a diluent. Examples of suitable diluents include the inert gases, such as nitrogen, argon and helium.

On contact of the carbon monoxide and dimethyl ether with the catalyst under carbonylation reaction conditions, the carbonylation reaction is initiated and methyl acetate is produced as a reaction product. Hydrogen is largely unconsumed in the carbonylation reaction.

The catalyst employed in the present invention may be any zeolite which is effective to catalyse the carbonylation of dimethyl ether with carbon monoxide in the presence of hydrogen to produce methyl acetate reaction product.

Zeolites are crystalline aluminosilicates which have framework structures constructed from tetrahedra of $SiO_4$ and $AlO_4$ that share vertices. Each framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC. A description of zeolites, their structure, properties and methods of synthesis can be found in The *Atlas of Zeolite Framework Types* (C. Baerlocher, W. M. Meier, D. H. Olson, 5$^{th}$ Ed. Elsevier, Amsterdam, 2001) in conjunction with the web-based version (http://www.iza-structure.org/databases/).

Suitably, for use in the present invention, a zeolite contains at least one channel or pocket (hereinafter collectively referred to as 'channels') which is defined by an 8-member ring. Preferably, an 8-member ring channel is interconnected with at least one channel defined by a ring with 10 or 12 members. The window size of the zeolite channel systems should be such that the reactant dimethyl ether and carbon monoxide molecules can diffuse freely in and out of the zeolite framework. Suitably, the window size of an 8-member ring channel is at least 2.5×3.6 Angstroms.

Preferred zeolites have a framework type selected from MOR, FER, OFF, CHA, GME and MFS.

Examples of zeolites of framework type MOR include mordenite. Examples of zeolites of framework type FER include ferrierite and ZSM-35. Examples of zeolites of framework type OFF include offretite. Examples of zeolites of framework type CHA include chabazite. Examples of zeolites of framework type GME include gmelinite. Examples of zeolites of framework type MFS include ZSM-57.

The zeolite for use in the present invention is preferably of framework type MOR, and in particular mordenite.

In addition to silicon and aluminium, zeolites for use in the present invention may have frameworks which comprise trivalent framework modifier elements such as one or more of boron, gallium and iron, preferably gallium. Suitably, the zeolite may be gallium mordenite.

Where aluminium atoms in the zeolite framework have been replaced by one or more of framework modifier elements, it is preferred that the ratio of silica to $X_2O_3$, where X is one or more trivalent elements selected from one or more of aluminium, boron, gallium and iron, is at least 5 but preferably less than or equal to 100, such as in the range of from 7 to 40, for example in the range 10 to 30.

For the purposes of the present invention, the silica to alumina molar ratio of a zeolite is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value. The bulk silica to alumina molar ratio (herein also termed "SAR") of a zeolite may vary. For example the SAR of a zeolite, such as mordenite may range from as low as 5 to over 90. The SAR of the zeolites for use in the present invention may suitably be in the range from 10 to 90:1, for example 20 to 60:1, such as 20 to 40:1.

Zeolites are widely available from commercial sources in synthetic form. Synthetic forms of zeolites include the sodium, ammonium and hydrogen forms of the zeolite. The ammonium form can be converted to the hydrogen form by known techniques, such as by calcining at elevated temperature. The sodium form can be converted to the hydrogen form by converting first to the ammonium form by ion-exchange with an ammonium salt, such as ammonium nitrate. Alternatively, zeolites may be synthesised using known techniques, for example a synthetic preparation of mordenite is described in U.S. Pat. No. 4,377,502.

Suitably, the zeolite utilised in the present invention is mordenite, preferably mordenite in the hydrogen form.

Zeolites, such as mordenites, may be synthesised by crystallising a synthesis mixture containing a source of alumina, a source of silica, a source of alkali metal and water.

If desired, the synthesis mixture may comprise an organic structure directing agent.

The organic structure directing agent may typically be a basic nitrogen compound, such as a quaternary ammonium compound, for example a tetraalkylammonium compound, such as a tetraethylammonium compound. Examples of tetraalkylammonium compounds include hydroxides and salts thereof, such as halides.

As a result of the crystallisation process to form a zeolite structure, the zeolite contains within its microporous structure the organic structure directing agent used in the synthesis mixture. The crystalline structure essentially wraps around the organic structure directing agent and the zeolite pores become blocked with molecules of the structure directing agent. The presence of the organic structure directing agent within the pores of the zeolite is thought to reduce or obviate the catalytic activity of a zeolite. Thus, typically, prior to use as a catalyst, an as-synthesised zeolite is treated to remove the organic structure directing agent from the zeolite. This is generally accomplished by calcining or heating the as-synthesised zeolite at elevated temperature, typically at temperatures of 200° C. and above.

Alternatively, zeolites, such as mordenites, can be synthesised from a synthesis mixture which does not comprise an organic structure directing agent.

In general, it is less costly and therefore desirable to manufacture zeolites without the use of organic structure directing agents. However, Applicant has found that the use of zeolites, and in particular mordenites, which have been prepared from synthesis mixtures which do not include organic structure directing agents, provide low selectivities and productivities to methyl acetate product in processes for the carbonylation of dimethyl ether which are operated throughout under hydrogen-rich conditions, that is with a molar excess of hydrogen.

Advantageously, the present invention provides for improved catalytic performance in processes for the carbonylation of dimethyl ether which are carried out under hydrogen-rich conditions, and, in particular improved catalytic performance in such processes of zeolite catalysts which have been synthesised without the aid of an organic structure directing agent.

Preferably, zeolites utilised in the present invention has been prepared from a synthesis mixture which does not comprise an organic structure directing agent. In particular, zeolites utilised in the present invention are mordenites which have been prepared from a synthesis mixture which does not comprise an organic structure directing agent. In particular, a zeolite for use in the present invention, such as a mordenite, is prepared from a synthesis mixture of a source of alumina, a source of silica, a source of alkali metal and water.

The sources of the silica, alumina and alkali or alkaline earth metal may be those conventionally used in zeolite synthesis mixtures. Representative of silica sources are colloidal silica, precipitated silica, silica gel, fumed silica and solid silica, silicon-containing compounds, such as silicic acid, metal silicates, such as sodium silicate and metallosilicates including aluminosilicates, for example, sodium aluminosilicate.

The source of alumina may be provided by a variety of sources, including activated alumina, alumina trihydrate, gamma alumina, and water soluble aluminium salts, such as aluminium sulphate, aluminium nitrate, hydrated aluminium hydroxides and aluminates, such as sodium aluminate or other metal aluminates.

It will be understood that each of the silica and alumina utilised in the synthesis mixture for preparing a zeolite can be supplied by one or more initial reagents. For example, silica can be supplied by an aqueous solution of sodium hydroxide or an aqueous solution of sodium silicate.

The sources of the alkali or alkaline earth metal include alkali metal or alkaline metal salts readily soluble in water, such as sodium aluminate or sodium silicate or in the form of hydroxides, such as alkali metal hydroxides, preferably, sodium hydroxide The components of the synthesis mixture can be added to water in any order.

In order to maintain a predetermined composition in the zeolite it will generally be preferable to employ starting materials of known purity and composition so that composition control is maintained.

The components are brought together in defined proportions in water to compose a zeolite-forming aqueous synthesis mixture. The synthesis mixture may be hydrothermally treated (with or without pressure) for a time and at a temperature to promote crystallisation. Suitably, the synthesis mixture is maintained until crystals of the zeolite are formed, for example, for a period of from 6 to 500 hours at elevated temperature, for example at a temperature of 80° C. to 210° C. At lower temperatures, for example 80° C., the crystallisation time is longer.

Suitably, the synthesis mixture is maintained until crystals of the zeolite are formed, for example for a period of from 6 to 500 hours at elevated temperature, for example at a temperature of 80° C. to 210° C.

Typically, the crystalline zeolite is formed in solution and can be recovered by standard means, such as by centrifugation or filtration, washed with water, suitably with deionised or distilled water, and dried. The synthetic zeolite crystallises as a fine powder which exhibits an x-ray diffraction pattern characteristic of that particular type of zeolite.

Zeolites containing alkali or alkaline earth metal, typically sodium are preferably treated to reduce the alkali/alkaline earth metal content thereof. Suitable treatments include conventional ion exchange procedures with replacing cations. Ion exchange may be carried out one or more times by contacting the zeolite with an aqueous solution containing the replacing cations. In general, ion exchange is conducted at temperatures in the range 25 to 100° C. for a suitable time interval, for example 1 to 6 hours. The degree of the ion-exchange can be varied by changing the time of the contact, concentration of the replacing cation solution and temperature.

Typical replacing cations include hydrogen and ammonium ions. Preferably ion-exchange is conducted with a source of ammonium cations such as an ammonium salt, for example, ammonium nitrate or ammonium chloride.

Following contact with an aqueous salt solution of the desired replacing cation, the zeolite may be washed with water and dried to produce a dry zeolite having the replacing cations occupying the alkali/alkaline earth metal sites.

Subsequent to being dried, the zeolite may be calcined to convert some or all of the ammonium cations to hydrogen cations.

Suitably, zeolites utilised in the present invention are in the hydrogen or ammonium form, preferably in the hydrogen form.

A preferred zeolite for use in the present invention is a mordenite in the hydrogen form and, more preferably a mordenite which has been prepared from a synthesis mixture which does not include an organic structure directing agent.

A zeolite employed in the present invention may optionally be ion-exchanged or otherwise loaded with one or more metals, such as one or more of copper, silver, nickel, iridium, rhodium, platinum, palladium and cobalt.

Zeolites are commercially available or otherwise synthetically prepared as fine crystalline powders and are typically further modified to enhance their properties for use in catalytic reactions, such as by forming the zeolites into shaped particles such as extrudates, pellets or beads. Processes for forming zeolites into shaped particles are well-known in the art and may be accomplished by forming a gel or paste of the zeolite powder with the addition of a suitable binder material and then extruding the gel or paste into the desired shape and then dried. Zeolite powders may also be formed into particles without the use of a binder.

Conveniently, a zeolite for use in the present invention may be composited with a binder, for example an inorganic oxide or a clay. Preferred binder materials are selected from aluminas, alumina-silicas and silicas, for example boehemite type alumina. However other inorganic oxides such as titanias, zirconias and magnesias may also be used. Suitable clays include bentonite and kieselguhr.

The relative proportions of a zeolite and the binder may vary widely but suitably, the zeolite may be present in the final catalyst in an amount of 10% to 90% by weight of the catalyst, preferably in an amount of 10% to 65% by weight of the catalyst.

The composited zeolite-binder mixture can be extruded to form the desired type of catalyst particle and optionally may be subjected to a thermal treatment to cure the binder to improve catalyst strength and attrition resistance. Thus, prior to use in carbonylation processes of the present invention, a composited zeolite may be calcined at elevated temperature, for example at temperatures of at least 500° C. The calcination may be carried out in an inert atmosphere, such as in nitrogen or helium or an oxidising atmosphere, such as in air or oxygen. The duration of the calcination may be, for example from about 10 minutes to 10 hours.

Suitably, a catalyst for use in the present invention is a mordenite composited with an alumina binder.

Dimethyl ether employed in the carbonylation process may be substantially pure dimethyl ether. In commercial practice, dimethyl ether is produced by the catalytic conversion of synthesis gas in the presence of methanol synthesis and methanol dehydration catalysts. This catalytic conversion results in a product which is predominantly dimethyl ether but it may also contain some methanol. In the present invention, the dimethyl ether may comprise small amounts of methanol provided that the amount of methanol is not so great as to inhibit the production of the methyl acetate reaction product.

Suitably, the dimethyl ether comprises 5 wt % or less, such as 1 wt % or less of methanol.

Diluents may be included in the dimethyl ether. Examples of suitable diluents include nitrogen, argon and helium.

Suitably, the concentration of dimethyl ether is in the range of from 0.1 to 20 mol %, such as 1.5 mol % to 15 mol % based on the total components of the gaseous feeds to the carbonylation reaction.

Preferably, dimethyl ether is present in the carbonylation process in the vapour phase.

As water can inhibit the carbonylation of dimethyl ether to produce methyl acetate the carbonylation process is preferably carried out under substantially anhydrous conditions. Suitably therefore, to limit the presence of water in the carbonylation process, all reactants, including dimethyl ether, and carbon monoxide, hydrogen and the catalyst are dried prior to their use in the process. Suitably, the carbonylation process is carried out with a water concentration of less than 1 mol %, based on the total gaseous feed to the carbonylation process, preferably less than 0.5 mol %, more preferably less than 0.2 mol %, and most preferably less than 0.1 mol %

Suitably, each of step (i) and step (ii) is carried out at a temperature of from about 200° C. to 350° C., such as from about 240° C. to 320° C., for example from about 250° C. to 310° C., preferably from about 260° C. to 300° C.

The carbonylation process may be carried out at pressures greater than atmospheric pressure. Thus, suitably, each of step (i) and step (ii) is carried out at a total pressure in the range of from 1 to 100 barg, such as from about 10 to 100 barg, for example from about 20 to 80 barg.

Desirably, the carbonylation process is carried out at a temperature in the range of from about 240° C. to 320° C. and a total pressure of from about 20 to 80 barg.

Suitably, each of step (i) and step (ii) is carried out at a total gas hourly space velocity (GHSV) of from 500 to 40,000 $h^{-1}$, such as 2,000 to 20,000 $h^{-1}$.

Preferably, the carbonylation process is carried out substantially in the absence of halides, such as iodide. By the term 'substantially' is meant that the total halide, for example, iodide content of the gaseous feeds to the reaction and the catalyst is less than 500 ppm, preferably less than 100 ppm.

If desired, dimethyl ether, hydrogen and carbon monoxide may be contacted with a guard bed immediately before a bed of catalyst so as to remove impurities therefrom. Suitable guard beds include alumina.

Desirably, the carbonylation is carried out as a vapour phase process, for example as a fixed bed process. Where the carbonylation is operated as a vapour phase process, the feedstock(s), prior to entering a reaction zone, may be in the liquid phase. However, prior to contact with the zeolite catalyst, it may be desired to volatilise liquid phase components, for example by use of a pre-heater.

The carbonylation process may be carried out in a reaction zone by passing a gaseous feed of dimethyl ether, carbon monoxide and hydrogen, through one or more fixed beds of the zeolite catalyst maintained at the desired reaction temperature. It is, of course understood that a reaction zone may be one or more separate reactors with suitable means therebetween to assure that the desired reaction temperature is maintained at the entrance to each reactor.

Prior to use, the catalyst may be activated, for example by heating the catalyst to the desired reaction temperature, and over any desired period of time, under one or more of carbon monoxide, hydrogen and inert gases such as nitrogen and helium.

The carbonylation of dimethyl ether with carbon monoxide produces methyl acetate as a reaction product. The carbonylation reaction product stream may also comprise additional components such as one or more of unreacted dimethyl ether, unreacted carbon monoxide and hydrogen.

Methyl acetate may be recovered from the reaction product by any suitable means. Suitably, the reaction product is removed from a reaction zone in the form of a vapour and is condensed to a liquid fraction comprising methyl acetate and a non-condensable gas fraction. The gas and liquid fractions may then be separated using known means such as knock-out drums or tangential inlet drums.

Methyl acetate recovered from the reaction product may be sold as such or it may be utilised in downstream chemical processes. For instance, some or all of the recovered methyl acetate may be converted to acetic acid, for example by a hydrolysis process. Hydrolysis processes are known in the art, and include, for example reactive distillation in the presence of an acidic catalyst.

Thus in some or all embodiments of the present invention, the process comprises the additional steps of recovering methyl acetate from the carbonylation process and converting some or all of the recovered methyl acetate to acetic acid.

The carbonylation process (comprising the first and second steps) may be operated as a continuous or a batch process, preferably as a continuous process.

The present invention will now be illustrated with reference to the following non-limiting Examples.

Example A

Not in Accordance with the Invention

The carbonylation reaction was carried out in a reactor of a pressure flow reactor unit consisting of 16 identical reactors of the type described in WO 2005063372. The reactor (internal diameter of 9.2 mm) was fitted with an internal tube of diameter 3.2 mm. On a dry mass basis (determined by loss on ignition of the catalyst measured by heating the catalyst from room temperature to 600° C. at a ramp rate of about 30° C. per minute), approximately 2 g (3 ml) of catalyst diluted with 3 ml of corundum (particle size 125 to 160 microns) was placed in the reactor on top of a 10 cm bed of corundum (particle size of 125-160 microns). An 11 cm bed of corundum (particle size of 125-160 microns) was placed on top of the catalyst bed. The reactor was pressurised to a total pressure of 70 bar with a 4 to 1 molar mixture of carbon monoxide and hydrogen at a flow rate of 12 l/h and then heated at 2° C./min to a temperature in the range 280° C. to 300° C. and held at this temperature for a period of 3 to 5 hours, after which the carbon monoxide/hydrogen feed was changed to a carbonylation reaction feed of carbon monoxide, dimethyl ether (DME) and hydrogen at a total gas hourly space velocity of 4000 $h^{-1}$ and a molar ratio of hydrogen to carbon monoxide of 2. The reaction was allowed to run for at least 160 hours with the carbonylation gas feed compositions given in Table 1 below. The exit stream from the reactor was passed periodically to a gas chromatograph to determine the concentration of reactants and carbonylation products.

In this Example A, the catalyst employed was a commercially available H-mordenite (silica:alumina molar ratio of 20) zeolite composited with 20 wt % alumina in the form of cylindrical extrudates having a diameter of 1.6 mm. An organic structure directing agent was not used in the preparation of the zeolite.

The carbonylation process was conducted throughout under a molar excess of hydrogen.

TABLE 1

| Time period (hours) | DME (mol %) | CO (mol %) | $H_2$ (mol %) | $CO:H_2$ molar ratio |
|---|---|---|---|---|
| 3-164 | 10 | 30 | 60 | 1:2 |

The space time yields of the carbonylation reaction and the selectivities of dimethyl ether to methyl acetate are shown in Table 1A below. Space time yields (STY) were calculated as acetic acid equivalents per liter of catalyst per hour. Acetic acid equivalents are determined by multiplying the STY for methyl acetate production by 0.81 [i.e. molecular weight (acetic acid)/molecular weight (methyl acetate)].

TABLE 1A

| Time (hours) | Average STY ($g \cdot l^{-1} h^{-1}$) | Average Selectivity (%) |
|---|---|---|
| 0-20 | 15 | 7 |
| 20-40 | 29 | 16 |
| 40-60 | 32 | 20 |
| 60-80 | 33 | 23 |
| 80-100 | 33 | 26 |
| 100-120 | 34 | 28 |
| 120-140 | 34 | 30 |
| 140-160 | 36 | 33 |

Example 1

Example A was repeated using the carbonylation gas feed compositions given in Table 2 below. For an initial period of 215 hours the carbonylation reaction was conducted with a molar excess of carbon monoxide and thereafter with a molar excess of hydrogen.

TABLE 2

| Time period (hours) | DME (mol %) | CO (mol %) | $H_2$ (mol %) | $CO:H_2$ molar ratio |
|---|---|---|---|---|
| 3-5 | 6 | 75.2 | 18.8 | 4:1 |
| 5-215 | 10 | 72.0 | 18.0 | 4:1 |
| 215-379 | 10 | 30 | 60 | 1:2 |

Figure 1:
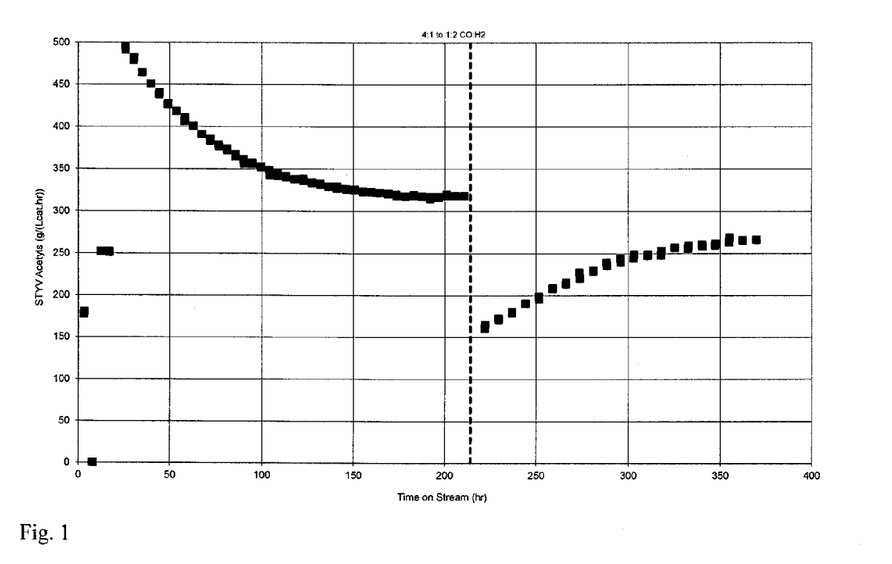
FIG. 1 depicts the STY in acetic acid equivalents (g/lcat·hr) versus time on stream for a carbonylation of dimethyl ether conducted with an initial molar ratio of carbon monoxide:hydrogen of 4:1 which is thereafter decreased to a molar ratio of 1:2.
Figure 2:
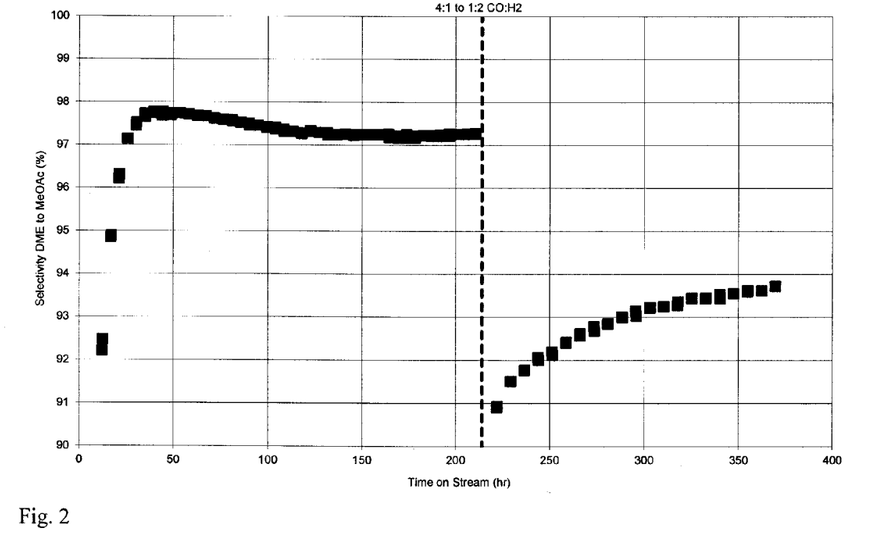
FIG. 2 depicts the selectivity (%) to methyl acetate versus time on stream for a carbonylation of dimethyl ether conducted with an initial molar ratio of carbon monoxide:hydrogen of 4:1 which is thereafter decreased to a molar ratio of 1:2.

The space time yields and the selectivities of dimethyl ether to methyl acetate obtained in this Example are shown in FIGS. 1 and 2.

As can be seen from an inspection of FIGS. 1 and 2, the space time yields and selectivities achieved using the process of the present invention are materially higher than those obtained in Example A, in which the carbonylation reaction was conducted throughout with a molar excess of hydrogen. Thus, high levels of hydrogen may be employed provided that initially the reaction is conducted with a molar excess of carbon monoxide.

Example 2

Example A was repeated using the carbonylation gas feed compositions given in Table 3 below and the catalyst was utilised in pellet form (500-650 microns). For an initial period of 265 hours the carbonylation reaction was conducted with a molar excess of carbon monoxide and thereafter it was conducted with a molar excess of hydrogen.

TABLE 3

| Time period (hours) | DME (mol %) | CO (mol %) | $H_2$ (mol %) | $CO:H_2$ molar ratio |
|---|---|---|---|---|
| 3-5 | 0 | 67 | 33 | |
| 5-7 | 6 | 62.7 | 31.3 | 2:1 |
| 7-265 | 10 | 60 | 30 | 2:1 |
| 265-267 | 6 | 31.3 | 62.7 | 1:2 |
| 267-432 | 10 | 30 | 60 | 1:2 |

Figure 3:
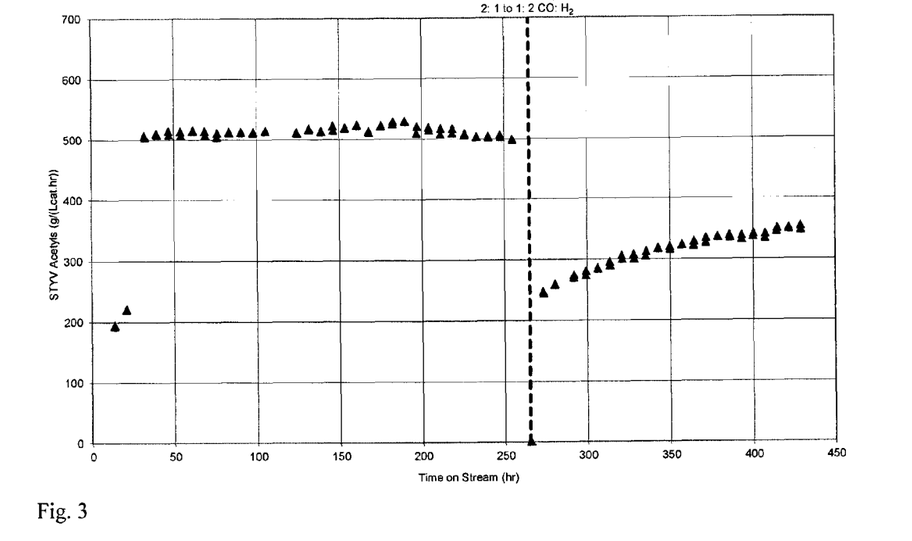
FIG. 3 depicts the STY in acetic acid equivalents (g/lcat·hr) versus time on stream for a carbonylation of dimethyl ether conducted with an initial molar ratio of carbon monoxide:hydrogen of 2:1 which is thereafter decreased to a molar ratio of 1:2.
Figure 4:
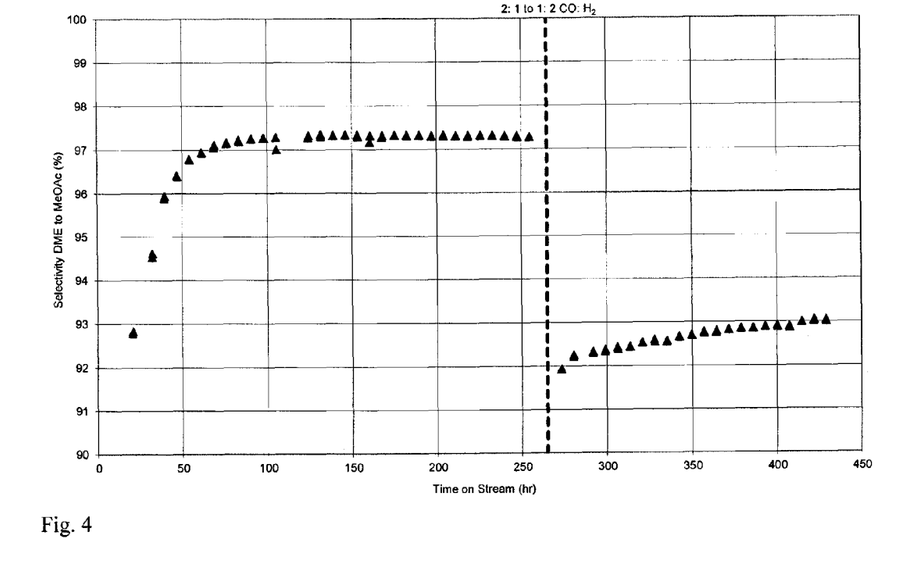
FIG. 4 depicts the selectivity (%) to methyl acetate versus time on stream for a carbonylation of dimethyl ether conducted with an initial molar ratio of carbon monoxide:hydrogen of 2:1 which is thereafter decreased to a molar ratio of 1:2.

The space time yield and selectivity (dimethyl ether to methyl acetate) results for this Example are shown in FIGS. 3 and 4. As can be seen from an inspection of FIGS. 3 and 4, the space time yields and selectivities are significantly higher than those achieved in Example A in which the reaction was conducted throughout with a molar excess of hydrogen.

Example 3

Carbonylation reactions, Reactions A and B were conducted using CO to $H_2$ molar ratios of 1:2 and 4:1 in a pressure flow reactor unit consisting of 16 identical parallel isothermal co-current tubular reactors of the type described in, for example WO2006107187. The reactors were arranged in 4 blocks of 4 reactors, each block having an independent temperature control. 100 microliters of the mordenite catalyst used in Example A was loaded onto a metal sinter (20 microns pore size) within a reactor. 100 microliters of gamma alumina was placed on top of the catalyst and the remainder of the reactor was filled with carborundum. The catalyst was activated by heating it at atmospheric pressure at a ramp rate of 5° C./min to a temperature of 300° C. under $N_2$ at a flow rate of 3.1 mL/min. After 1 hour at 300° C., the $N_2$ gas was replaced by a gaseous mixture of carbon monoxide, hydrogen and helium (molar ratio of 1:2:0.1) at a total gas flow rate of 6.1 ml/min. The reactor was then pressurised to 60 barg and left to equilibrate for two hours at which point activation of the catalyst was considered complete. The gaseous mixture was then replaced by a carbonylation gas feed having a composition and $CO:H_2$ molar ratio shown in Table 4 below.

TABLE 4

| | CO (mol %) | $H_2$ (mol %) | DME (mol %) | He (mol %) | $CO_2$ (mol %) | $CO:H_2$ molar ratio |
|---|---|---|---|---|---|---|
| Reaction A | 29.1 | 58.1 | 5 | 2.8 | 5 | 1:2 |
| Reaction B | 69.7 | 17.5 | 5 | 2.8 | 5 | 4:1 |

Each carbonylation reaction was allowed to continue for 125 hours. The exit stream from the reactor was passed to an Interscience Trace gas chromatograph equipped with two TCD and one FID detectors: One TCD channel was equipped with two columns, a Carboxen 1010(2 m*0.32 mm) and a Carboxen 1010(28 m*0.32 mm). The other TCD channel was equipped with a Poraplot U (2 m*0.32 mm) and a Poraplot Q (12 m*0.32 mm) column. The FID channel equipped with a Rtx-1, 1 u (20 m*0.32 mm) and a Rtx-wax, 0.25 u (2 m*0.32 mm) column.

The space time yield and selectivity results for Reaction A carried out at a $CO:H_2$ molar ratio of 1:2 are shown in Table 5A and the results for Reaction B carried out at a $CO:H_2$ molar ratio of 4:1 are shown in Table 5B.

TABLE 5A

| Time (hours) | Average STY $(g \cdot l^{-1} h^{-1})$ | Average Selectivity (%) |
| --- | --- | --- |
| 0-20 | 53 | 12 |
| 20-40 | 73 | 15 |
| 40-60 | 89 | 18 |
| 60-80 | 90 | 19 |
| 80-100 | 91 | 18 |
| 100-115 | 95 | 19 |

TABLE 5B

| Time (hours) | Average STY $(g \cdot l^{-1} h^{-1})$ | Average Selectivity (%) |
| --- | --- | --- |
| 0-20 | 303 | 85.9 |
| 20-40 | 293 | 97.3 |
| 40-60 | 251 | 97.6 |
| 60-80 | 204 | 97.8 |
| 80-100 | 198 | 97.8 |
| 100-120 | 192 | 97.7 |
| 120-140 | 189 | 97.8 |
| 140-160 | 189 | 97.7 |

This Example demonstrates that, for a zeolite prepared without the aid of an organic structure directing agent, starting a carbonylation reaction under a molar excess of hydrogen results in poor catalytic performance which performance remains poor throughout the entire carbonylation reaction. In contrast for the same catalyst, a dramatic improvement in catalytic performance is achieved by starting the reaction up under a molar excess of carbon monoxide.

Example 4

Example A was repeated using the carbonylation gas feed compositions given in Table 6 below and the catalyst of Example A utilised in pellet form (500-650 microns). The reaction was carried out initially using an equimolar amount of carbon monoxide and hydrogen and subsequently with a molar excess of hydrogen.

TABLE 6

| Time period (hours) | DME (mol %) | CO (mol %) | $H_2$ (mol %) | $CO:H_2$ molar ratio |
| --- | --- | --- | --- | --- |
| 3-7 | 0 | 50 | 50 | |
| 7-9 | 6 | 47 | 47 | 1:1 |
| 9-150 | 10 | 45 | 45 | 1:1 |
| 150-294 | 10 | 30 | 60 | 1:2 |

Figure 5:
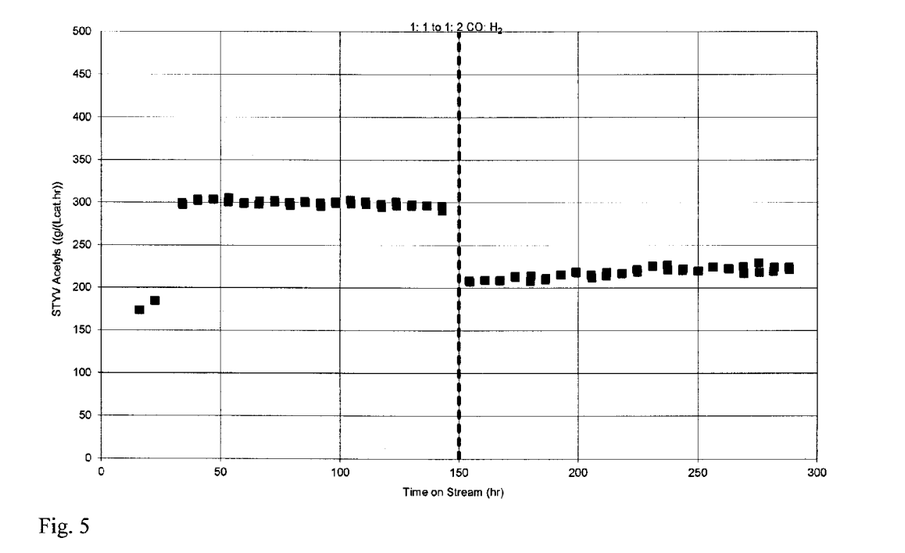
FIG. 5 depicts the STY in acetic acid equivalents (g/lcat·hr) versus time on stream for a carbonylation of dimethyl ether conducted with an initial molar ratio of carbon monoxide:hydrogen of 1:1 which is thereafter decreased to a molar ratio of 1:2.
Figure 6:
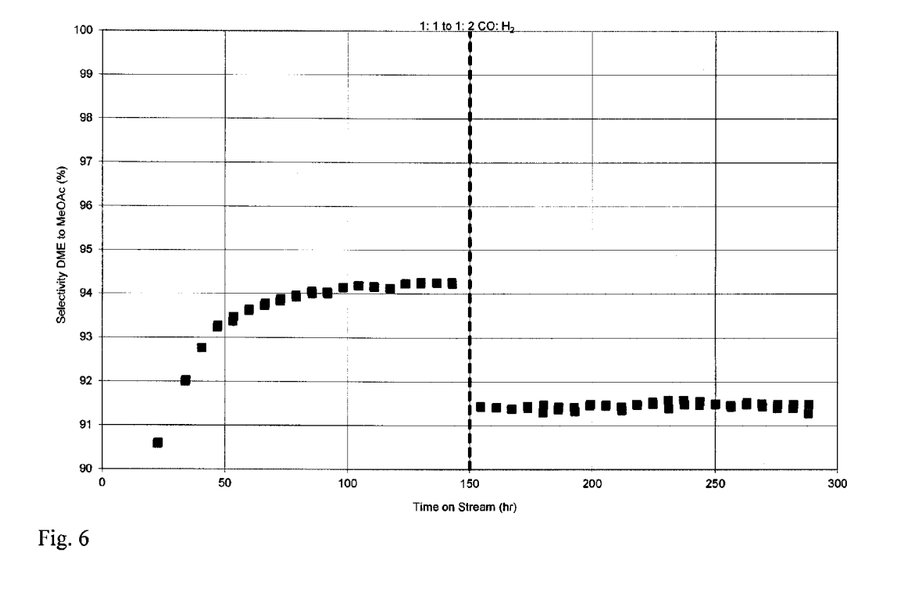
FIG. 6 depicts the selectivity (%) to methyl acetate versus time on stream for a carbonylation of dimethyl ether conducted with an initial molar ratio of carbon monoxide:hydrogen of 1:1 which is thereafter decreased to a molar ratio of 1:2.

The space time yield and the selectivity (dimethyl ether to methyl acetate) results for this Example are shown in FIGS. 5 and 6. As can be seen from an inspection of FIGS. 5 and 6, the space time yields and selectivities obtained by the initial use of an equimolar amount of carbon monoxide and hydrogen are materially higher than those achieved in Example A where the reaction is conducted throughout with a molar excess of hydrogen.

Example 5

Example A was repeated using as catalyst H-mordenite zeolite composited with alumina. The mordenite was prepared from a synthesis mixture which comprised tetraethyl ammonium bromide as the organic structure directing agent. Prior to use in the carbonylation reaction the structure directing agent was removed from the zeolite structure by calcination.

The space time yields and the selectivities of dimethyl ether to methyl acetate obtained in the reaction are shown in Table 7 below.

TABLE 7

| Time (hours) | Average STY $(g \cdot l^{-1} h^{-1})$ | Average Selectivity (%) |
| --- | --- | --- |
| 0-20 | 436 | 85 |
| 20-40 | 440 | 91 |
| 40-60 | 434 | 92 |
| 60-80 | 435 | 93 |
| 80-100 | 439 | 93 |
| 100-120 | 444 | 93 |
| 120-140 | 441 | 93 |
| 140-160 | 450 | 94 |

Example 6

Example A was repeated using the catalyst of Example 5 and the carbonylation gas feed compositions as shown in Table 8 below.

TABLE 8

| Time period (hours) | DME (mol %) | CO (mol %) | $H_2$ (mol %) | $CO:H_2$ molar ratio |
| --- | --- | --- | --- | --- |
| 3-5 | 6 | 75.2 | 18.8 | 4:1 |
| 5-215 | 10 | 72.0 | 18.0 | 4:1 |
| 215-379 | 10 | 30 | 60 | 1:2 |

Figure 7:
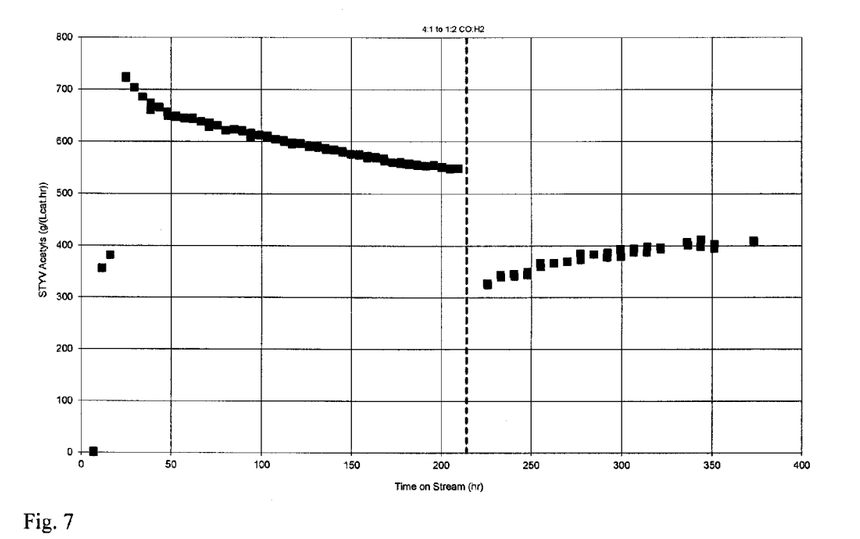
FIG. 7 depicts the STY in acetic acid equivalents (g/lcat·hr) versus time on stream for a carbonylation of dimethyl ether conducted with an initial molar ratio of carbon monoxide:hydrogen of 4:1 which is thereafter decreased to a molar ratio of 1:2 using a catalyst prepared with an organic structure directing agent.
Figure 8:
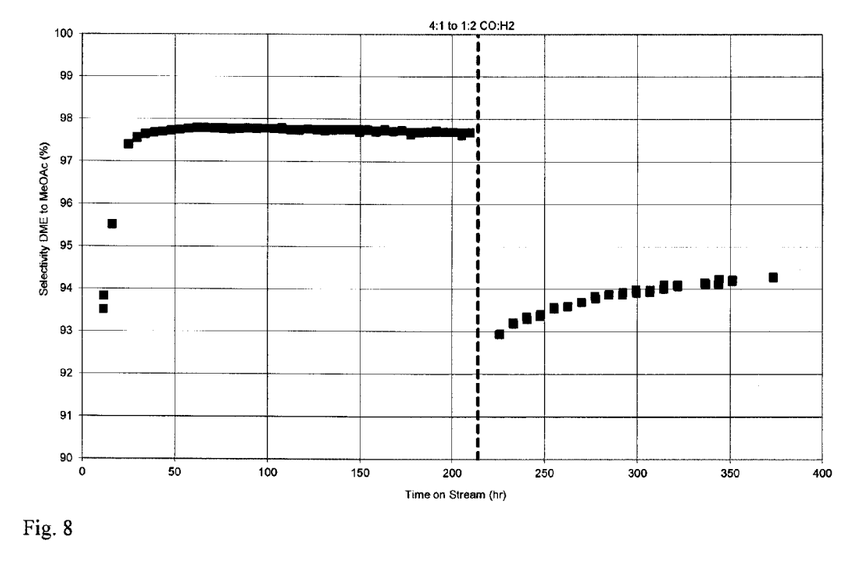

The space time yields and the selectivities of dimethyl ether to methyl acetate obtained in this Example are shown in FIGS. 7 and 8.

The invention claimed is:

1. A process for preparing methyl acetate by the carbonylation of dimethyl ether with carbon monoxide in the presence of hydrogen and a zeolite catalyst wherein, in a first step the carbonylation is conducted with a carbon monoxide to hydrogen molar ratio of at least 1 and in a second and subsequent step, the carbonylation is conducted with a hydrogen to carbon monoxide molar ratio of greater than 1.

2. A process for improving the performance of a zeolite catalyst in the preparation of methyl acetate by the carbonylation of dimethyl ether with carbon monoxide in the presence of hydrogen and said catalyst wherein, in a first step the carbonylation is conducted with a carbon monoxide to hydrogen molar ratio of at least 1 and in a second and subsequent step, the carbonylation is conducted with a hydrogen to carbon monoxide molar ratio of greater than 1.

3. A process according to claim 1 wherein in the first step the molar ratio of carbon monoxide to hydrogen is in the range 1 to 15.

4. A process according to claim 3 wherein in the first step the molar ratio of carbon monoxide to hydrogen is in the range 2 to 4.

5. A process according to claim 1 wherein in the second step the molar ratio of hydrogen to carbon monoxide is in the range 1.05 to 5.

6. A process according to claim 1 wherein in the second step the molar ratio of hydrogen to carbon monoxide is in the range 2 to 5.

7. A process according to claim 1 wherein in the first step the molar ratio of carbon monoxide to hydrogen is in the range 2 to 4 and in the second step the molar ratio of hydrogen to carbon monoxide is in the range 1.05 to 5.

8. A process according to claim 1 wherein in the first step the molar ratio of carbon monoxide to hydrogen is in the range 1 to 4 and in the second step the molar ratio of hydrogen to carbon monoxide is in the range 2 to 5.

9. A process according to claim 1 wherein the first step is conducted for a period of from 10 minutes to 300 hours.

10. A process according to claim 1 wherein the zeolite contains at least one channel which is defined by an 8-member ring.

11. A process according to claim 10 wherein the 8-member ring channel is interconnected with at least one channel defined by a ring with 10 or 12 members.

12. A process according to claim 11 wherein the zeolite is of a framework type selected from the group consisting of MOR, FER, OFF and GME.

13. A process according to claim 12 wherein the zeolite is of framework type MOR and is mordenite.

14. A process according to claim 13 wherein the mordenite is in the hydrogen form.

15. A process according to claim 1 wherein the zeolite is ion-exchanged or otherwise loaded with one or more metals.

16. A process according to claim 1 wherein the zeolite has been prepared from a synthesis mixture which does not comprise an organic structure directing agent.

17. A process according to claim 1 wherein the zeolite is composited with a binder.

18. A process according to claim 17 wherein the binder is selected from aluminas, silica-aluminas and silicas.

19. A process according to claim 1 wherein the catalyst is mordenite composited with an alumina binder.

20. A process according to claim 1 wherein the catalyst is in the form of shaped particles selected from extrudates, pellets and beads.

21. A process according to claim 1 wherein each of the first and second steps is carried out at a temperature is in the range of from 200° C. to 350° C.

22. A process according to claim 1 wherein each of the first and second steps is carried out at a total pressure in the range 20 to 80 barg.

23. A process according to claim 1 wherein the carbon monoxide to hydrogen molar ratio in the first step is adjusted for the second step in a single stage.

24. A process according to claim 1 wherein the carbon monoxide to hydrogen molar ratio in the first step is adjusted for the second step in two or more stages.

25. A process according to claim 1 wherein the first step is carried out during start-up of the process.

26. A process according to claim 1 wherein the process is carried out with a water concentration of less than 1 mol % based on the total gaseous feed to the process.

27. A process according to claim 1 wherein the source of carbon monoxide and hydrogen is a synthesis gas.

28. A process according to claim 1 wherein the carbonylation process is carried out as a vapour phase process.

29. A process according to claim 1 wherein the carbonylation process comprising the first and second steps is operated as a continuous process.

30. A process according to claim 1 which includes the additional steps of recovering methyl acetate from the carbonylation process and converting some or all of the recovered methyl acetate to acetic acid.

* * * * *